United States Patent
Bartle (10) Patent No.: US 6,678,396 B2
(45) Date of Patent: Jan. 13, 2004

(54) METHOD FOR THE NON-INVASIVE MEASUREMENT OF PROPERTIES OF MEAT

(75) Inventor: Colin Murray Bartle, Wilton (NZ)

(73) Assignee: Institute of Geological & Nuclear Sciences Limited, Lower Hunt (NZ)

( * ) Notice: Subject to any disclaimer, the term of this patent is extended or adjusted under 35 U.S.C. 154(b) by 0 days.

(21) Appl. No.: 10/316,751

(22) Filed: Dec. 11, 2002

(65) Prior Publication Data

US 2003/0091144 A1 May 15, 2003

Related U.S. Application Data

(63) Continuation of application No. PCT/NZ01/00108, filed on Jun. 11, 2001.

(51) Int. Cl.[7] .................................................. G06K 9/00
(52) U.S. Cl. ...................................... 382/110; 378/98.9
(58) Field of Search ................................. 382/100, 110, 382/128, 132; 378/53, 54, 62, 98.9

(56) References Cited

U.S. PATENT DOCUMENTS 4,029,963 A * 6/1977 Alvarez et al. ............. 250/360
4,168,431 A * 9/1979 Henriksen ................ 250/358 R
4,171,164 A * 10/1979 Groves et al. ............... 366/152
6,052,433 A * 4/2000 Chao ........................ 378/98.9
6,449,334 B1 * 9/2002 Mazess et al. ................ 378/53

FOREIGN PATENT DOCUMENTS

| AU | 702503 B2 | * | 2/1999 | .......... G01N/23/08 |
| WO | WO 96/31770 A1 | * | 10/1996 | .......... G01N/23/083 |
| WO | WO 01/09596 A1 | * | 2/2001 | .......... G01N/23/087 |
| WO | WO 01/29557 A2 | * | 4/2001 | .......... G01N/33/12 |

* cited by examiner

*Primary Examiner*—Andrew W. Johns
(74) *Attorney, Agent, or Firm*—Thomas R. Vigil; Welsh & Katz, Ltd.

(57) ABSTRACT

The properties of meat are assessed using a non-invasive dual-energy X-ray absorption scanner. Two images or arrays of the values representative of the intensities of the X-rays at two energy levels are produced (1). These are then processed to determine properties such as the chemical lean, fat percentage, weight, presence of contaminants and the tenderness of the scanned meat (2–5). The meat assessment includes a correction step to overcome unwanted instrumental effects.

36 Claims, 11 Drawing Sheets

METHOD FOR THE NON-INVASIVE MEASUREMENT OF PROPERTIES OF MEAT

This application is a continuation of international application number PCTNZ01/00108, filed Jun. 11, 2001, published as WO 01/96844 on Dec. 20, 2001.

FIELD OF INVENTION

The invention comprises a method for the non-invasive measurement of the properties of meat using a dual energy x-ray absorption scanner.

BACKGROUND

An important property of meat is meat yield Meat yield is a measure of the percentage of a block of meat that is fat and the percentage of the block of meat that is chemical lean. Together fat and chemical lean make up the block of meat. Other important properties of meat include weight of the meat, meat tenderness, the effective atomic number of the meat and the amount of contamination in the meat.

Dual energy x-ray absorption scanners produce output intensities of two different x-ray energies in different ways. An x-ray tube working at one voltage, for example 150 keV, will produce x-rays with energies from 150 keV down to 0 keV. To select two groups of x-ray energies from this distribution two detectors may be used where each detector is capable of measuring one of the two groups of x-ray energies required. These detectors may be string-like detectors housed above the conveyor belt in a line across the scanner surface. The two detectors may be placed one on top of the other, or alternatively side by side above the scanner surface. A second method for producing a dual energy output is to rapidly switch the x-ray source between two energy levels. In an x-ray absorption scanner of this form a single detector may be used to detect x-ray intensities at both x-ray energies.

SUMMARY OF INVENTION

It is He object of the present invention to provide an improved or at least alternative method for the non-invasive measurement of properties of meat.

In broad terms in one aspect the invention comprises method for assessing a property or properties of meat including the steps of scanning the meat using a dual energy x-ray absorption scanner to produce two images or arrays of values representative of the intensities of the x-rays at two energy levels, and processing the images or arrays of values to determine at least one property of the scanned meat.

Preferably the method includes the step of correcting the assessment for instrumental effects that may affect the assessment of the meat property or properties.

Preferably the method includes the step of assessing the mass centroid along at least one axis of the images or arrays of values and using this in the correction for instrumental effects.

Preferably the method includes the step of assessing the mass of the meat using the images or arrays of values and using this in the correction for instrumental effects.

Preferably the method includes processing only pixels or data points in the high x-ray intensity image or array that fall below a threshold value.

The images or arrays of values may also be stored for fixture retrieval and/or reprocessing.

The method for assessing a property or properties of meat may further include the steps of converting at least one red-green-blue image of the changes in atomic number into an intensity image and assessing the meat tenderness from the at least one intensity image.

The method for assessing a property or properties of meat according may further include the steps of individually extracting each component of a red-green-blue image of the changes in atomic number, processing each extracted component into an intensity image, analysing each image to determine changes in image intensity, producing a binary array for each component based on the changes in intensity, and assessing meat tenderness from the variations of the binary arrays.

In broad terms in a further aspect the invention includes an apparatus for assessing a property or properties of meat comprising a dual energy x-ray absorption scanner for scanning the meat and arranged to produce two images or arrays of values representative of the intensities of the x-rays at two energy levels, and an associated computer system arranged to process the images or arrays of values to determine at least one property of the scanned meat.

Preferably the computer system of the apparatus is arranged to correct the assessment for instrumental effects that may affect the assessment of the meat property or properties.

Preferably the computer system of the apparatus is arranged to assess the mass centroid along at least one axis of the images or arrays of values and use this in the correction for instrumental effects.

Preferably the computer system of the apparatus of the invention is arranged to assess the mass of the meat using the images or arrays of values and use this in the correction for instrumental effects.

Preferably the computer system of the apparatus of the invention is arranged to process only pixels or data points in the high x-ray intensity image or array that fall below a threshold value.

The apparatus of the invention may also be arranged to store the images or arrays of values for future retrieval and/or reprocessing.

The computer system of the apparatus of the invention may be further arranged to convert at least one red-green-blue image of the changes in atomic number into an intensity image and assess the meat tenderness from the at least one intensity image.

The computer system of the apparatus of the invention may be further arranged to individually extract each component of a red-green-blue image of the changes in atomic number, process each extracted component into an intensity image, analyse each image to determine changes in image intensity, produce a binary array for each component based on the changes in intensity, and assess meat tenderness from the variations of the binary arrays.

BRIEF DESCRIPTION OF DRAWINGS

The method of the invention will be further described with reference to the accompanying drawings, wherein.

DETAILED DESCRIPTION

The dual energy x-ray absorption scanner operates by producing a beam of x-rays in a source module positioned below the scanner surface in scanner housing. The source is collimated to a narrow fan shape that passes through the item to be scanned and is intercepted by a line detector. The scanner includes suitable radiation shielding.

Typically the detector is a line detector including a string of small independent detectors positioned across the scanner above the scanner surface, and supported by detection equipment. The detectors detect x-ray intensities at two different energy levels, hence the term dual energy x-ray absorption scanner. The detectors and detection equipment enable the energies of the x-rays to be detected after transmission through the item on the scanner surface.

In the method of the invention meat is scanned by passing it through a dual energy x-ray absorption scanner. This scanner preferably uses an energy source to produce x-rays with energy of around 140 keV. The x-ray source is preferably located below the scanner surface and the x-rays are collimated to form a fan or line across the scanner surface. The x-rays penetrate the meat and pass to detectors located above the scanner surface. The detection system used by the scanner preferably responds to split out two groups of x-ray energies with mean values of about 100 keV and 80 keV. This information is passed to the output of the scanner in terms of the intensity of the high and low energy x-ray beams after passing through the meat.

Note that although the energy source is described as being set at 140 keV this is by way of example only. Scanners with different energies can be used. For example it is conceivable that container loads of meat may be scanned using a scanner with energies of up to 500 keV.

The effective atomic number of a material is calculated as a sum of terms of the form $C_Z W_Z Z$ divided by the sum of the terms of form $C_Z W_Z$, where Z is the atomic number of each contributing element in the material matrix, $C_Z$ is the corresponding number of atoms per unit mass and $W_Z$ is a corresponding weight representing the relative measurement bias for this element. The measurement bias is determined from the physical principles underlying the measurement process. Many gauge systems employing x-rays have an enhanced sensitivity to higher atomic number elements, because the photo-absorption process is proportional to $Z^n/A$, where A is the nucleon number and "n" is theoretically as high as 5.

The detection system used by the scanner preferably responds to split out two groups of x-ray energies with means of about 100 keV and 80 keV This information is passed to the output of the scanner in terms of the intensity of the high and low energy x-ray beams after passing through the meat The algorithm used for determining the effective atomic number of a substance passed through the scanner is of the form:

Effective Atomic Number=$A*((H-L)/L)+B*H+C$ where H and L represent the high energy beam and low energy beam intensities respectively and A, B and C are coefficients. A, B and C are initially calculated by comparison of the dual energy x-ray absorption scanner output and the laboratory calculated effective atomic number. These coefficients are specific to the scanner used and also to the application for which the scanner is used In use when A, B and C are known the effective atomic number may be calculated using the above equation.

Other equations may also be used to determine the effective atomic number of a material from the high and low energy x-ray beams detected after passing through the material. These variations include the following equations;

Effective Atomic Number=$A1*((H-L)/H)+B1*H+C$

Effective Atomic Number=$A2*((H-L)/(H+L))+B2*H+C$

Effective Atomic Number=$A3*((H-L)/L)+B3*L+C$

Effective Atomic Number=$A4*((H-L)/H)+B4*L+C$

Effective Atomic Number=$A5*((H-L)/(H+L))+B5*L+C$ where the A, B and C coefficients are different for each equation. Other similar variations may also be used.

Once the meat has been scanned intensity images can be produced representing the intensities of the high and low energy x-ray beams. These images can then be processed to produce information about the scanned meat such as the effective atomic number of the meat described above.

Chemical lean is a measurement of the meat and fat content of a box of meat. The higher the chemical lean measurement the less fat is present in the box of meat, Chemical lean measurements range from 0 to 100.

Figure 1A:
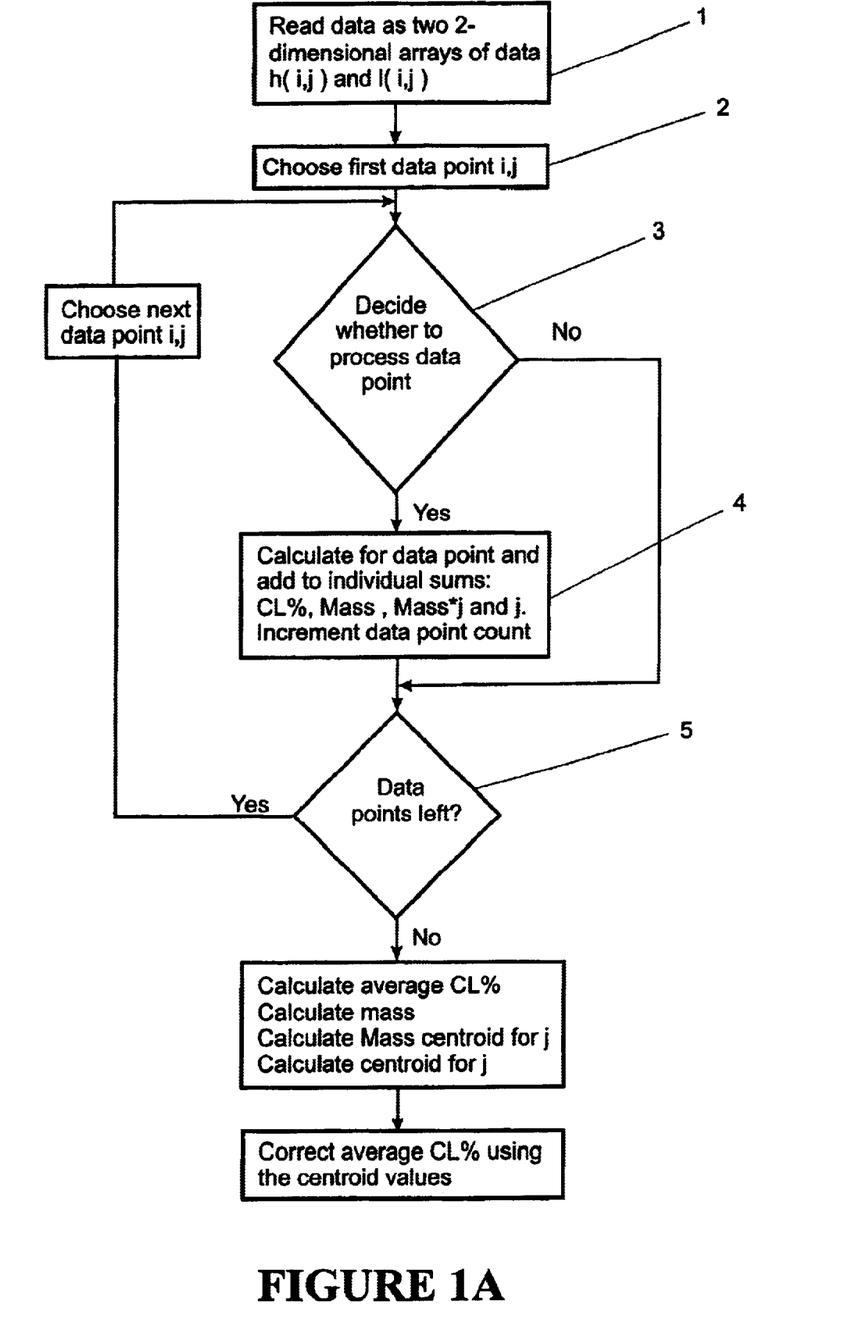
FIG. 1A is a flow chart showing the processing of data produced by scanning meat to produce a chemical lean percentage measurement.

FIG. 1A shows a preferred form algorithm for determining the chemical lean of meat from x-ray intensity images of the meat after scanning by a dual energy x-ray absorption scanner. At 1 both images are read into a processor as two dimensional arrays with the same indices. Here h[i,j] represents the high energy x-ray intensity image and l[ij] represents the low energy x-ray intensity image of the scanned meat In this case i represents the direction or relative motion between the meat and the scanner and j represents the direction across the box. However other representations of i and j could be used without departing from the scope of the invention. In the data arrays j is set to range between 0 and jmax, where jmax is an integer.

At 2 the first data point of each array is selected, The next decision is whether the data point should be processed. This occurs at decision box 3. Each data point is processed if its high energy intensity value is below a threshold limit. Any data point representing a space that is not covered by the mean is not processed. If the meat does not cover a spot then the x-rays pass directly to the detector Rough only the material on which the meat is placed, producing a high intensity value at the detector. By only processing data points which fall below a threshold level the orientation of the meat on the scanner surface does not pose problems to the processing to the intensity data.

If the high x-ray intensity level falls below the threshold value then the data point is processed in step 4. For each data point the data point chemical lean percentage, mass of the meat at the data point, mass multiplied by the data point index j and the data point index j are stored. The data point chemical lean percentage is calculated as $$\text{Data point } CL\% = 100 - \left(KA * \frac{h[i, j] - l[i, j]}{l[i, j]} + KB * h[i, j] + KC\right)$$

where KA, KB, and KC are constants. As can be seen by comparing this equation to the effective atomic number equation above, the data point chemical lean percentage is determined from the effective atomic number like assessment of the meat at the data point. Again other equations like the alternative effective atomic number equations above could be used to form part of the chemical lean percentage equation. Again the coefficients may differ for each variation of the equation.

The data point mass is calculated as $$\text{Data point mass} = KMA * \log\left(\frac{KMB}{l[i, j]}\right)$$

where KMA and KMB are constants.

In step 5 the algorithm queries whether it has finished processing all of the data points in the arrays. If the algorithm has not processed all data points it shifts to the next data point and returns to step 3 to determine whether to process the data point. When the algorithm has finished processing all data points the average chemical lean percentage, mass, mass centroid for the j index and the centroid for the j index are calculated.

Using the mass centroid for the j index and the centroid of the j index a corrected chemical lean percentage can be calculated. Before this is calculated the centroid Y (CY) value is calculated as the sum of j values divided by the number of data points processed n, then divided by jmax. The mass centroid Y (MCY) value is also calculated as the sum of the data point mass times the j index divided by the sum of the data point mass and then divided by jmax. The corrected chemical lean percentage can then be calculated as Corrected CL%=CL%+(KCA*(MCY−CY)+KCB)

where KCA and KCB are constants.

This corrected chemical lean percentage value is compensated for uneven meat distribution in the box in the direction of the detector array and allows a more accurate estimate of the percentage of chemical lean to be made, The correction takes into account the variation in x-ray path geometry (angle and length) from the x-ray source passing through the meat to the detector array and other instrumental effects. The percentage fat of the meat can be determined using a similar set of equations or from the chemical lean percentage.

Figure 1B:
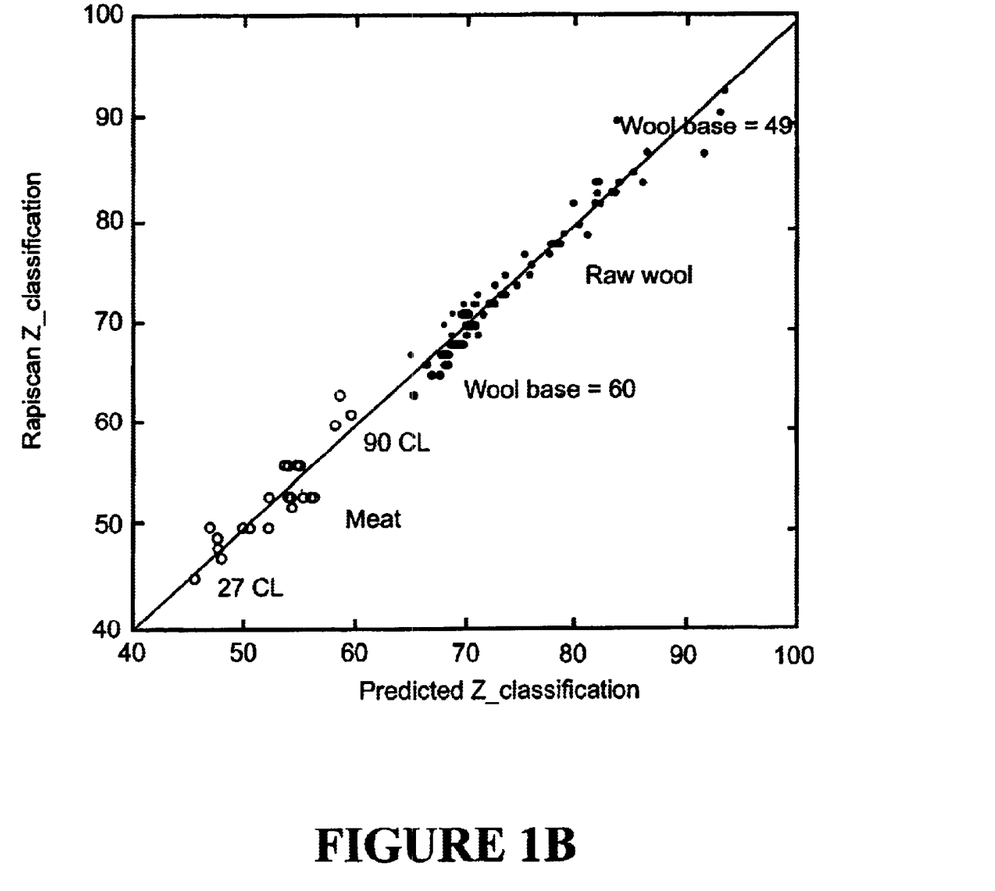
FIG. 1B is a graph showing the correlation of z-classification of meat scanned by a DEXA scanner and a standard scanner.

As described above a number like the effective atomic number can be calculated for the scanned meat and used in determination of the chemical lean of the meat. A chemical lean measurement response has been achieved that is proportional to the effective atomic number calculated from the output of the DEXA scanner for chemical lean measurements of between 60 and 100. This measurement response ranges from 20 to 100 chemical lean for standards. FIG. 1B shows the correlation of mew scanned using a DEXA scanner and another standard scanner. The chemical lean (CL) numbers on the graph show the proportional measurement of chemical lean and DEXA scanner measurements.

Figure 1C:
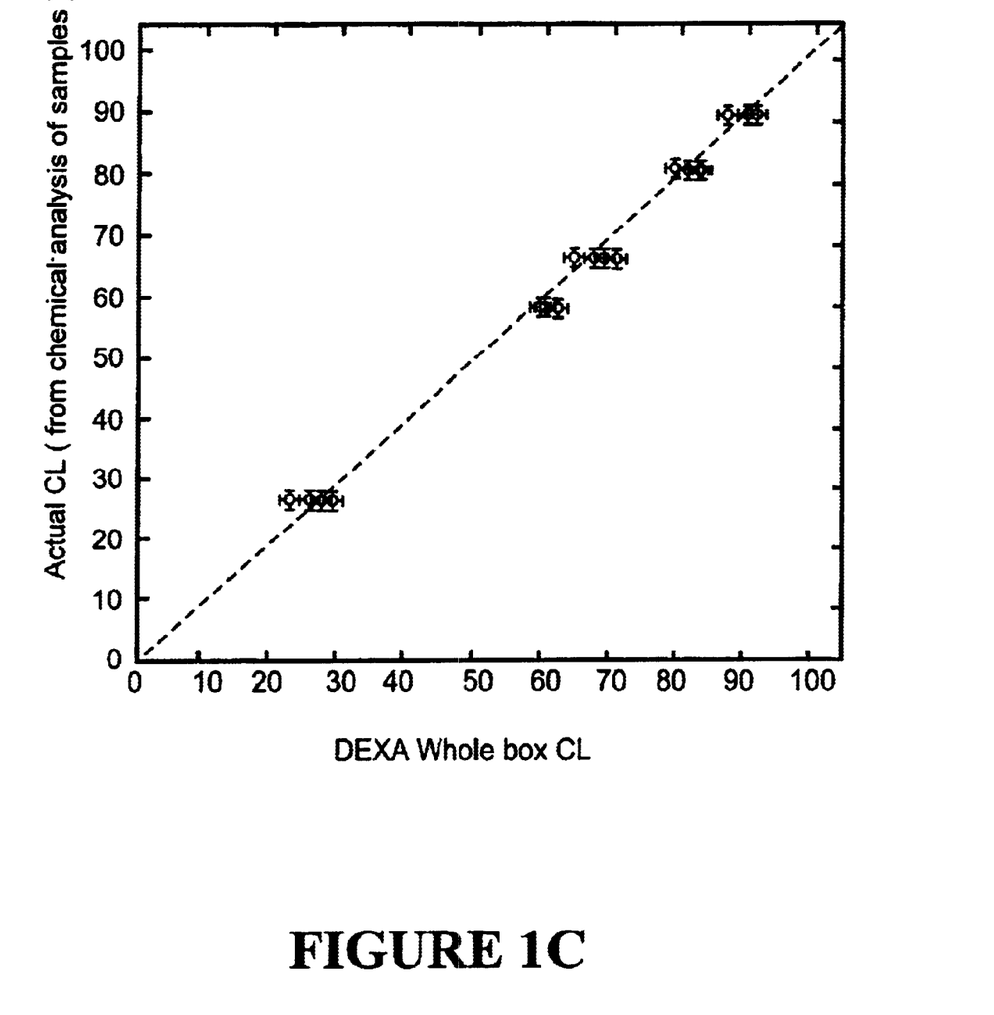
FIG. 1C is a graph showing calibration of software associated with a DEXA scanner so that the scanner can be used to determine chemical lean in meat.

FIG. 1C shows the results of calibration of a DEXA scanner so that the method of the invention can be used for determining the chemical lean of meat. The chemical lean of boxes of meat with weights of between 25 and 30 kilograms was determined by chemical sample analysis and then used to calibrate a computer attached to a DEXA scanner. This allowed calibration of the scanner and/or related software so that the scanner could be used to determine chemical lean values.

Figure 1D:
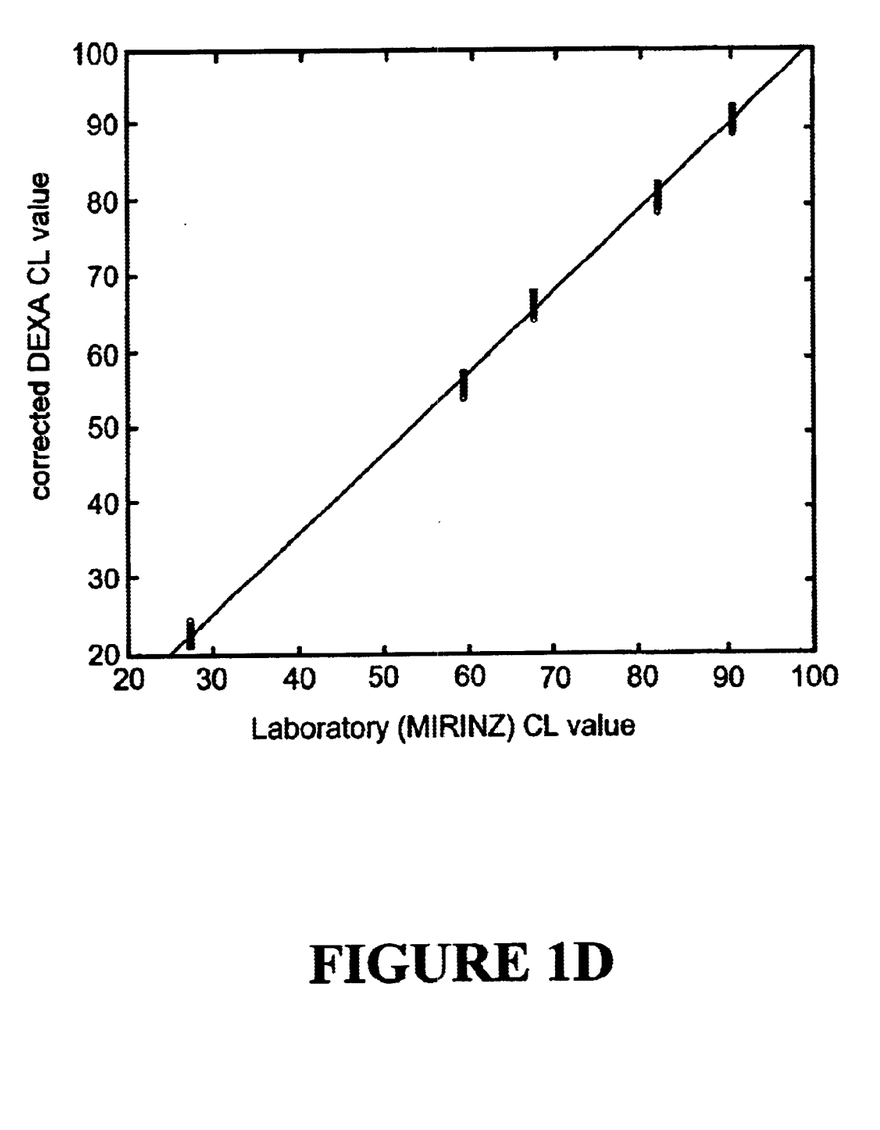
FIG. 1D is a graph showing the use of a DEXA scanner to determine chemical lean values for meat.
Figure 1E:
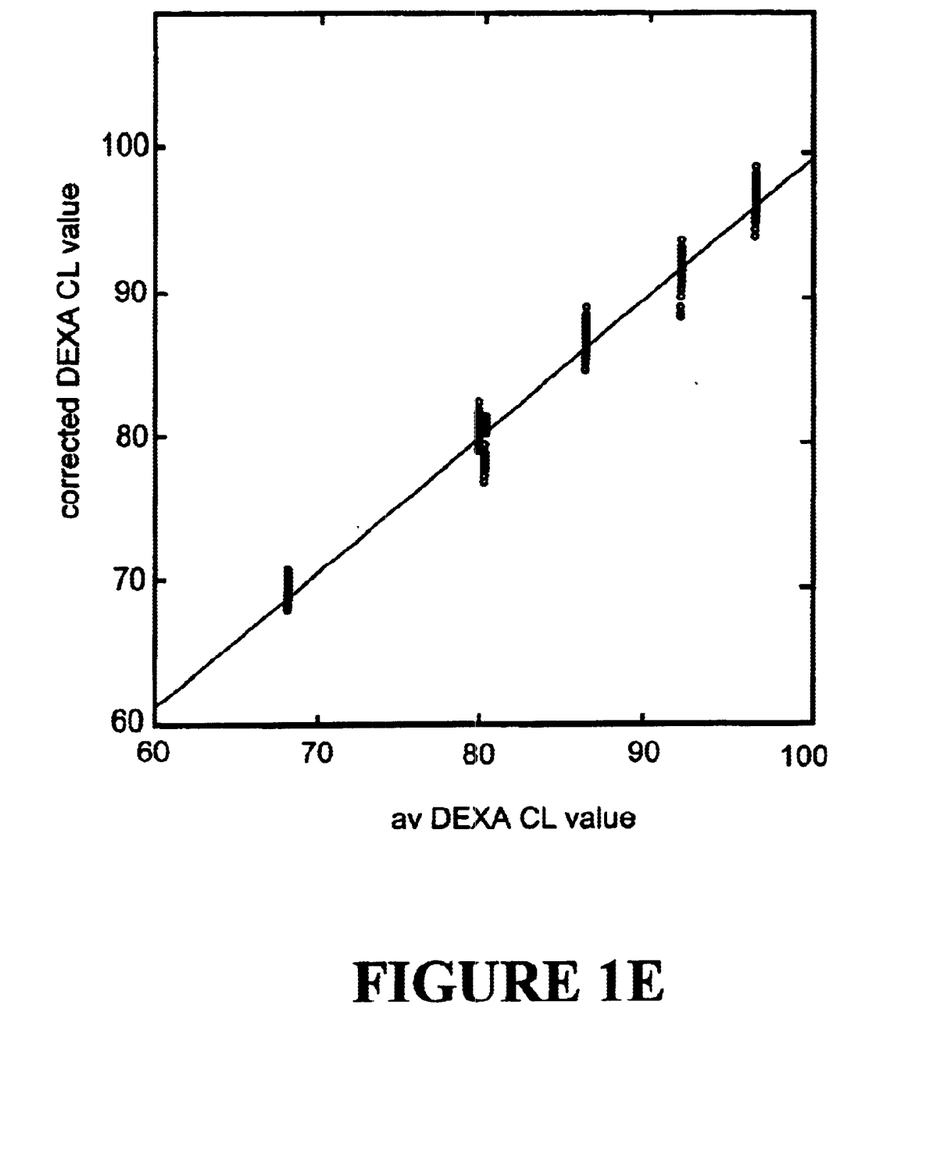
FIG. 1E is a graph showing the use of a DEXA scanner to determine chemical lean values for meat.

FIGS. 1D and 1E show the use of the DEXA scanner to determine chemical lean values for meat. FIG. 1D shows the assessed chemical lean output of a DEXA scanner after scanning a selection of homogenous meat boxes against the laboratory calculated chemical lean values, The software used for assessing the chemical lean value from the output of the DEXA scanner includes corrections for mass distribution variations. The average standard deviation of the DEXA chemical lean measurements is 0.8 CL.

FIG. 1E shows the average chemical lean values assessed from the output of a DEXA scanner plotted against the chemical lean values assessed from the output of a DEXA scanner and corrected for box mass distribution variations. Boxes used for this graph were fed through the scanner with different orientations. These measurements were made up to 50 times and resulted in an average standard deviation of about 1 CL. More trials have reproduced this result.

Figure 1F:
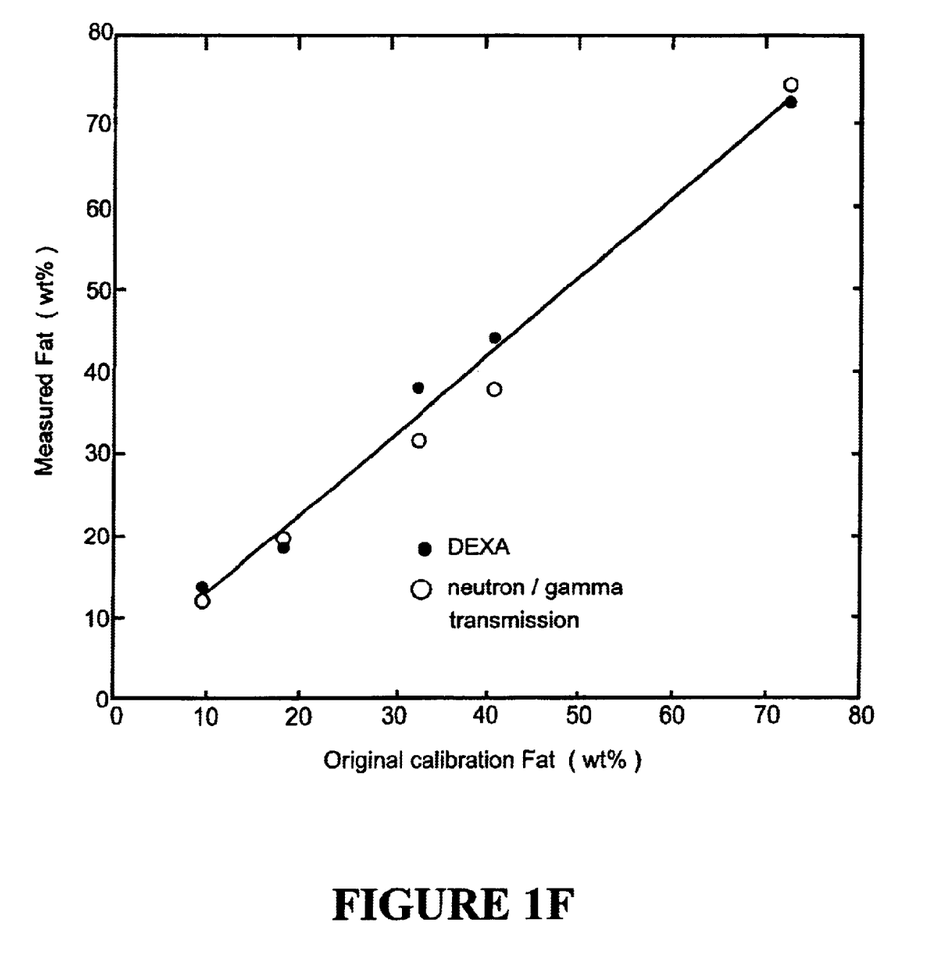
FIG. 1F is a graph showing the fat content of a sample of meat boxes.

FIG. 1F shows a graph of the percentage fat content by weight of a sample of 27 kg meat boxes (an industry standard size) using the dual energy x-ray absorption scanner method plotted against calibration values and the percentage fat content by weight of the sample as assessed using a neutron/gamma instrument. As can be seen in FIG. 1F meat scanned using the method of the invention provides an accurate representation of the percentage fat in a 27 kg meat box.

Figure 1G:
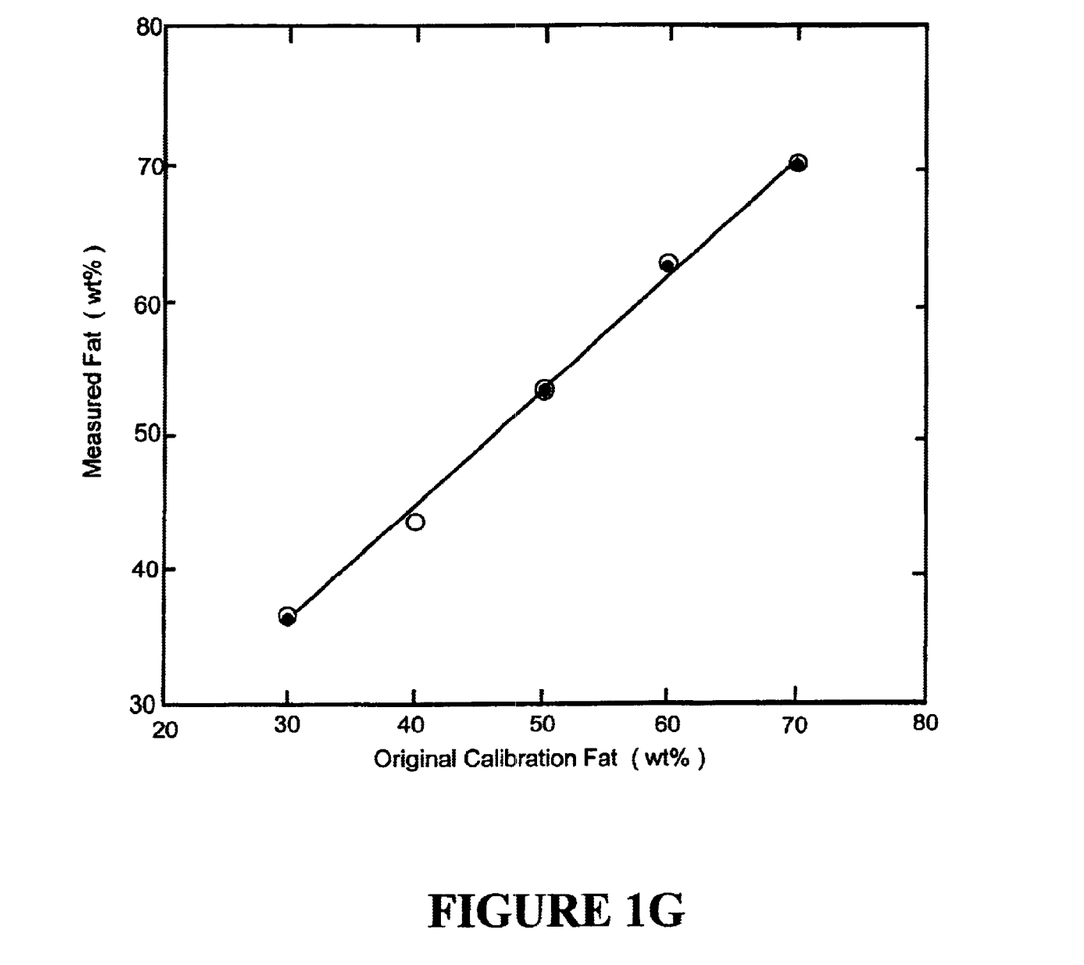
FIG. 1G is a graph showing the fat content of small samples of meat.

FIG. 1G shows a graph of percentage by weight fat calibration versus percentage by weight fat as measured using the method of the invention For this graph 120 ml packets of lamb and packets of combined lamb and beef were scanned. As can be seen from FIG. 1G meat scanned using the method of the invention provides an accurate representation as to the percentage fat in a 120 ml packet.

Contamination of meat may also be assessed using the method of the invention. Once the meat has been scanned the effective atomic number image or arrays of high and low x-ray energy intensity data produced can be scanned to detect any contamination in the meat. For example metal pieces and bone may be present in the meat. These contaminants have different atomic numbers to meat and fat and will show up as different intensities on the scanned image or in the data arrays and can be detected by either visually, electronically or otherwise scanning the image. Using a DEXA scanner contaminants with diameter of greater than 5 mm can be detected Contaminants in a box of meat may be detected once the images from the DEXA scanner have been further scanned and may also be counted and the location of each contaminant within the meat box stored.

Figure 1H:
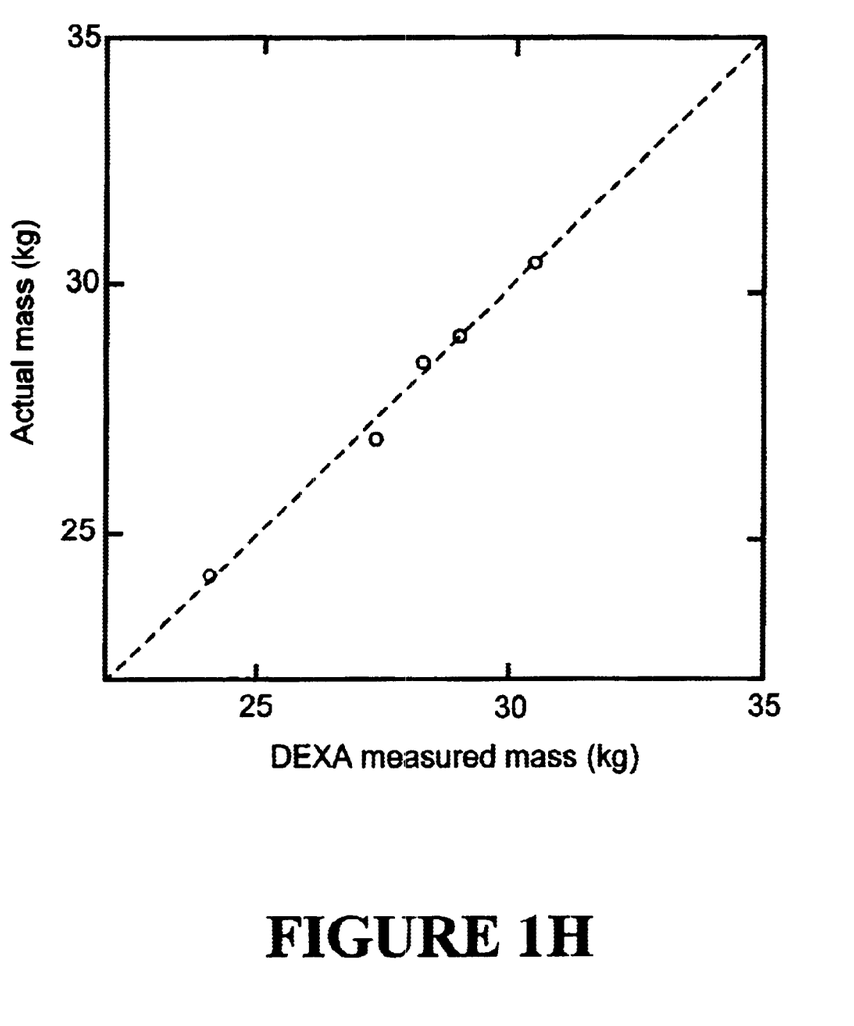
FIG. 1H is a graph showing the correlation between weights of meat boxes and weights determined by scanning the meat boxes.

The weight of the meat boxes may also be assessed using a DEXA scanner and the method of the invention. The attenuation of x-rays passing through the meat box is related to the total mass of product in the x-ray beam path. As the meat is scanned the attenuation of the x-rays passing through the meat may be measured and then combined to give the weight of the meat box. FIG. 1H shows the correlation between meat boxes weighed on scales and the weight of the boxes assessed using a DEXA scanner. As can be seen from this figure there is a good correlation between the two values showing that the weight can be accurately assessed by the DEXA scanner. It has been found experimentally that the DEXA scanner can be used to assess the weight of meat boxes (weighing between 20 and 35 kilograms) with a standard deviation of less than 100 g.

Once a property of the meat, such as chemical lean, weight or amount of contamination has been assessed the meat may be assigned a grade based on the assessment. More than one property may be assessed and a grade may be based on the assessment of more than one property of the meat. For example both the chemical lean (or percentage fat) and weight of the meat may be assessed or both the chemical lean (or percentage fat) and tenderness may be assessed.

Software to which the output of a DEXA scan of the meat is fed may be arranged to determine at least one of: the weight of the meat boxes, the number and location of contaminants in the box, the chemical lean of the meat in the box or the percentage fat of the meat in the box and the effective atomic number of the meat in the box. An associated computer system may also store the image produced from the DEXA scan for later access, preferably with information identifying the particular meat box, and preferably The farm from which the meat originated. Storing of the image in a database allows for subsequent retrieval and analysis if required. The software ideally takes into account small instrument effects in the DEXA scanner that may affect the calculations. Such instrumental effects include lateral position of the meat box on the conveyor passing through the scanner, scanner start-up and duty cycle effects and mass and chemical lean asymmetries in the meat box.

With the system of the invention it is also possible to analyse the image produced by the DEXA scanner to detect changes in the structure of the item and assess meat tenderness.

The output form the DEXA scanner may be produced in the form of a "false colour" image with different colours representing different ranges of atomic numbers. For example orange may represent atomic numbers between 1 and 10, green may represent atomic numbers between 11 and 20 and blue may represent atomic numbers greater than 20.

Using image processing techniques the image file can be split into pixel arrays one each for the red, green and blue components of the image. Each value in the array is then scaled to between 0 and 1 representing the intensity of the value with 0 equivalent to black or low intensity an 1 equivalent to white or high intensity. Three gray-scale intensity arrays then exist for the red-green-blue image, one for each component. The gray-scale intensity images are, in the preferred form, filtered to produce binary images comprising only 0's and 1's representing black and white respectively. To do this each array may be subjected to a non-linear function that sets the intensity value to zero if the value is below a threshold level and sets the intensity value to 1 if the value is above the threshold level. For example a typical threshold level is 0.5. Intensity values equal to the threshold level are arbitrarily assigned to eider 1 or 0. Once the gray-scale intensity array has been filtered the average intensity of the binary arrays is a measure of the contribution from the various atomic number ranges.

Figure 2A:
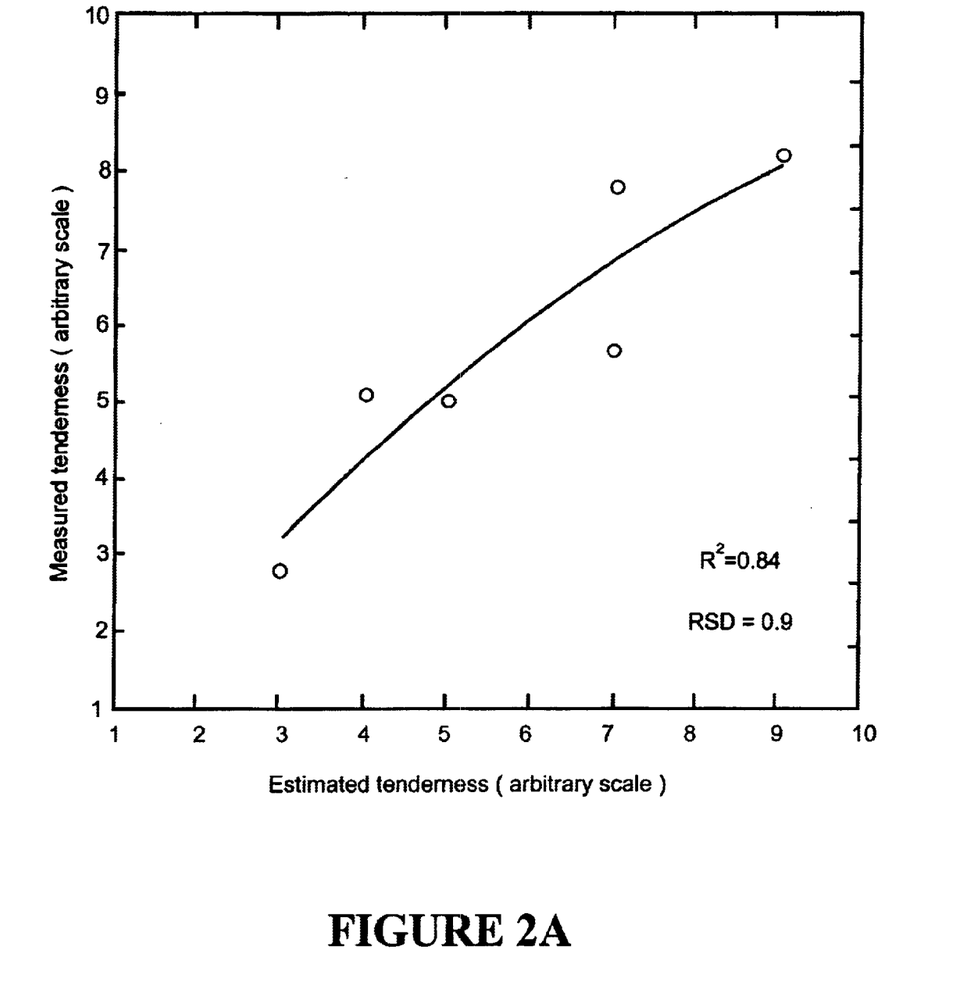
FIG. 2A is a graph of meat tenderness calculated using the method of the invention and actual values.

Correlations between the gray-scale intensities and the tenderness ordering were found. Small samples of meat (around 250 grams) were scanned by the DEXA scanner and the output image file transferred to a computer for image processing. FIG. 2A is a graph showing Me estimated tenderness plotted against the tenderness found using the method of the invention.

The tenderness found using the method of the invention is given by equation 1, which is based on the correlations between the gray-scale intensities and the tenderness ordering scale.

$$\text{Meat tenderness} = CRL*ri + CGL*gi + CBL*bi + C \qquad 1$$

where:
  ri is the average red intensity calculated from the filtered gray-scale red array,
  gi is the average green intensity calculated from the filtered gray-scale green array,
  bi is the average blue intensity calculated from the filtered gray-scale blue array,
  CRL is the red layer coefficient=−0.012,
  CGL is the green layer coefficient=0.056,
  CBL is the blue layer coefficient=−0.054, and
  C=8.9

Figure 2B:
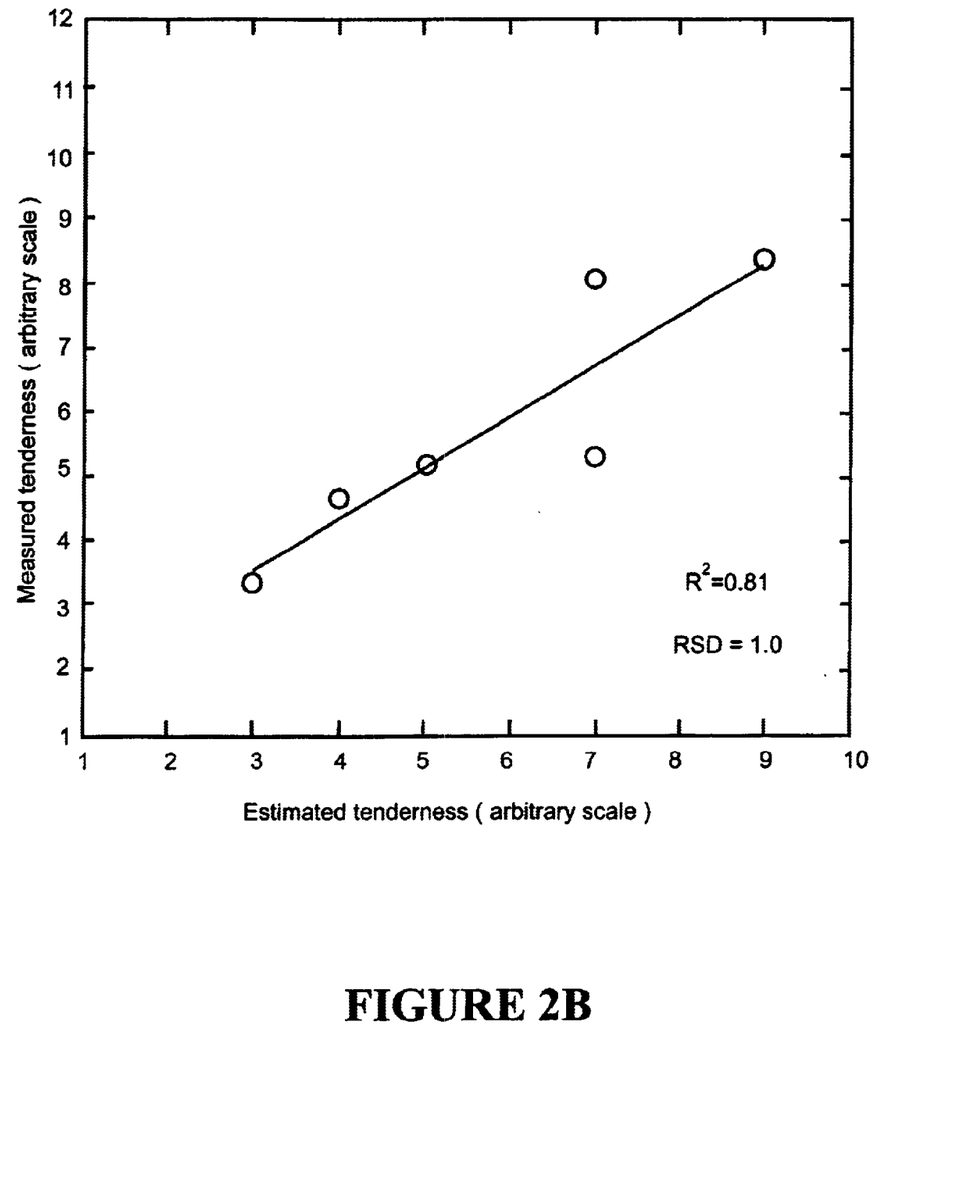
FIG. 2B is a graph of meat tenderness calculated using a method of the invention and actual values.

It is also possible to calculate the tenderness of meat by using the gray-scale information from a single colour component. FIG. 2B is a graph of estimated tenderness against measured tenderness using blue-layer information only. The equation used to calculate meat tenderness from blue-layer information is:

$$\text{Meat tenderness} = CBL*bi + C' \qquad 2$$

where
  bi is the average blue intensity calculated from the filtered gray-scale blue array,
  CBL is the blue layer coefficient=−0.025, and
  C'−8.42

This method has the advantage that errors caused by sample thickness, which are small for thin samples but increase as the thickness of the sample increases are avoided.

A second method to measure the tenderness of meat using a DEXA scanner measures changes in the texture of the images rather than gray-scale intensities To calculate the tenderness of meat using changes in intensity of the image the meat samples may be scanned using the DEXA scanner as described previously. The red-green-blue images are transferred to a computer for processing and split into component arrays Each component array is gray-scaled based on the intensity of the array elements as before. From the gray-scale intensity arrays regions of rapid intensity changes are found and linked as contour lines through the image array. The contour lines or edge structures may then be converted into binary images and the extent of the edge structures assessed through image standard deviations. The greater the image's standard deviation the greater the extent of the edge structures. This analysis appears to be independent of the overall image intensities. The standard deviations for each of the red-green-blue binary edge structure arrays are then used to calculate the tenderness of the meat using equation 3.

$$\text{Meat tenderness} = CRL*rsd + CGL*gsd + CBL*bsd + C \qquad 3$$

where
  rsd is the standard deviation of the bit edge structure array of the red component,
  gsd is tile standard deviation of the binary edge structure array of the green component,
  bsd is the standard deviation of the binary edge structure array of the blue component,
  CRL is the red layer coefficient=−0.29,
  CGL is the green layer coefficient=0.11
  CBL is the blue layer coefficient=0.005, and
  C=14.4

Figure 2C:
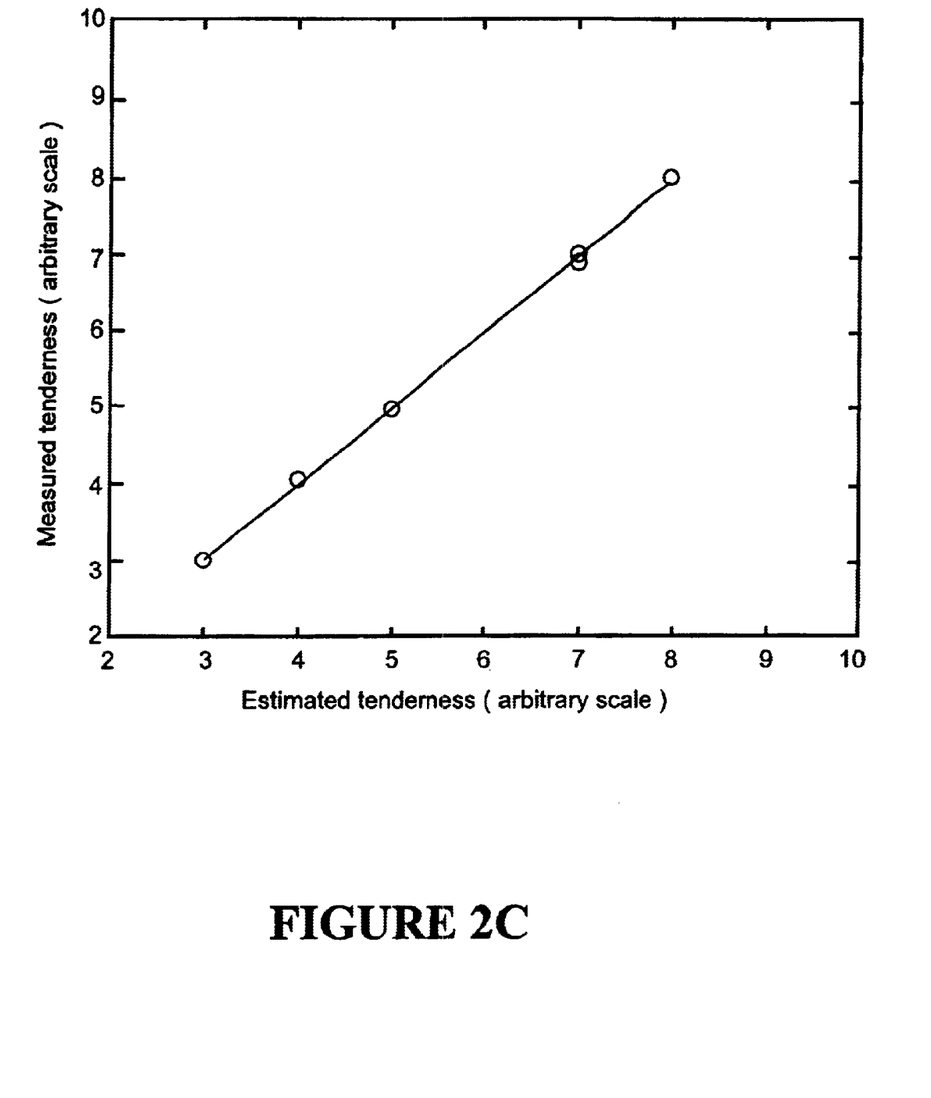
FIG. 2C is a graph of meat tenderness calculated using a method of the invention and actual values.

FIG. 2C is graph showing meat tenderness estimated using the subjective scale plotted against meat tenderness calculated using the method of edge structures as described above and with porterhouse steak allocated as 8 on the tenderness scale, The foregoing describes the invention including preferred forms thereof. Alterations and modifications as will be obvious to those skilled in the art are intended to be incorporated in the scope hereof as defined by the accompanying claims.

What is claimed is:

1. A method for assessing a property or properties of meat including the steps of:

scanning the meat using a dual energy x-ray absorption scanner to produce two images or arrays of values representative of the intensities of the x-rays at two energy levels, and processing the images or arrays of values using at least one equation from the group of:

effective atomic number=$A*((H-L) \div L)+B*H+C$ effective atomic number=$A*((H-L) \div H)+B*H+C$ effective atomic number=$A*((H-L) \div (H+L))+B*H+C$ effective atomic number=$A*((H-L) \div L)+B*L+C$ effective atomic number=$A*((H-L) \div H)+B*L+C$ effective atomic number=$A*((H-L) \div (H+L))+B*L+C$ data point $CL\%=100-(KA*(H-L) \div L+KB*H+KC)$ corrected $CL\%=CL\%+(KCA*(MCY-CY)+KCB)$ meat tenderness=$CRL*RI+CGL*GI+CBL*BI+C$ meat tenderness=$CBL*BI+C'$ meat tenderness=$CRL*RSD+CGL*GSD+CBL*BSD+C$ to determine at least one property of the scanned meat, where H represents an array of value or image of the x-rays at a first energy level, L represents an array of values or image of the x-rays at a second energy level, A, B. C, C', KA, KB, KC, KCA, KCB, CRL, CGL, CBL are constants, CL % is the chemical lean percentage of the meat, MCY is the mass centroid, CY is the y centroid, RI is the average red intensity calculated from a filtered gray-scale red array, GI is the average green intensity calculated from a filtered gray-scale green array, BI is the average blue intensity calculated from a filtered gray-scale blue array RSD is the standard deviation of a binary edge structure array of a red component, GSD is the standard deviation of a binary edge structure array of a green component, and BSD is the standard deviation of a binary edge structure array of a blue component.

2. A method for assessing a property or properties of meat according to claim 1 further including the step of correcting the assessment for instrumental effects that may affect the assessment of the meat property or properties.

3. A method for assessing a property or properties of meat according to claim 2 including the step of assessing the mass centroid along at least one axis of the images or arrays of values and using this in the correction for instrumental effects.

4. A method for assessing a property or properties of meat according to claim 2 including the step of assessing the mass of the meat using the images or arrays of values and using this in the correction for instrumental effects.

5. A method for assessing a property or properties of meat according to claim 2 including the step of assessing the centroid along at least one axis of the images or arrays of values and using this in the correction for instrumental effects.

6. A method for assessing a property or properties of meat according to claim 1 wherein the step of processing the images or arrays of values includes the step of determining whether pixels in the image or data points in the array of values fall below a threshold level in the high x-ray intensity image or array of values.

7. A method for assessing a property or properties of meat according to claim 6 including processing only pixels or data points in the high x-ray intensity image or array that fall below the threshold value.

8. A method for assessing a property or properties of meat according to claim 1 including the step of grading the meat based on the assessed property or properties of the meat.

9. A method for assessing a property or properties of meat according to claim 1 including the step of storing the images and/or arrays of values with an identifier in a database for future retrieval and/or reprocessing.

10. A method for assessing a property or properties of meat according to claim 1 wherein the assessed property is the chemical lean of the meat.

11. A method for assessing a property or properties of meat according to claim 1 wherein the assessed property is the percentage fat of the meat.

12. A method for assessing a property or properties of meat according to claim 1 wherein the assessed property is the weight of the meat.

13. A method for assessing a property or properties of meat according to claim 1 wherein the assessed property is contamination of the meat.

14. A method for assessing a property or properties of meat according to claim 1 wherein the assessed property is the tenderness of the meat.

15. A method for assessing a property or properties of meat according to claim 14 further including the steps of converting at least one red-green-blue image of the changes in atomic number into an intensity image and assessing the meat tenderness from the at least one intensity image.

16. A method for assessing a property or properties of meat according to claim 14 further including the steps of;

individually extracting each component of a red-green-blue image of the changes in atomic number;

processing each extracted component into an intensity image;

analysing each image to determine changes in image intensity;

producing a binary array for each component based on the changes in intensity; and assessing meat tenderness from the variations of the binary arrays.

17. A method for assessing a property or properties of meat according to claim 1 including carrying out said method to assess both the fat or chemical lean and weight.

18. A method for assessing a property or properties of meat according to claim 1 including carrying out said method to assess both the fat or chemical lean and tenderness.

19. Apparatus for assessing a property or properties of meat including a dual energy x-ray absorption scanner for scanning the meat and arranged to produce two images or arrays of values representative of the intensities of the x-rays at two energy levels, and an associated computer system arranged to process the images or arrays of values using at least one equation from the group of:

$$\text{effective atomic number} = A*((H-L) \div L) + B*H + C$$

$$\text{effective atomic number} = A*((H-L) \div H) + B*H + C$$

$$\text{effective atomic number} = A*((H-L) \div (H+L)) + B*H + C$$

$$\text{effective atomic number} = A*((H-L) \div L) + B*L + C$$

$$\text{effective atomic number} = A*((H-L) \div H) + B*L + C$$

$$\text{effective atomic number} = A*((H-L) \div (H+L)) + B*L + C$$

$$\text{data point } CL\% = 100 - (KCA*(H-L) \div L + KB*H + KC)$$

$$\text{corrected } CL\% = CL\% + (KCA*(MCY-CY) + KCB)$$

$$\text{meat tenderness} = CRL*RI + CGL*GI + CBL*BI + C$$

$$\text{meat tenderness} = CBL*BI + C'$$

$$\text{meat tenderness} = CRL*RSD + CGL*GSD + CBL*BSD + C$$

to determine at least one property of the scanned meat, where

H represents an array of values or image of the x-rays at a first energy level,

L represents an array of values or image of the x-rays at a second energy level, A, B, C, C', KA, KB, KC, KCA, KCB, CRL, CGL, CBL are constants, CL % is the chemical lean percentage of the meat, MCY is the mass centroid, CY is the y centroid, RI is the average red intensity calculated from a filtered gray-scale red array, GI is the average green intensity calculated from a filtered gray-scale green array, BI is the average blue intensity calculated from a filtered gray-scale blue array RSD is the standard deviation of a binary edge structure array of a red component, GSD is the standard deviation of a binary edge structure array of a green component, and BSD is the standard deviation of a binary edge structure array of a blue component.

20. Apparatus for assessing a property or properties of meat according to claim 19 wherein the associated computer system is further arranged to correct the assessment for instrumental effects that may affect the assessment of the meat property or properties.

21. Apparatus for assessing a property or properties of meat according to claim 20 wherein the associated computer system is further arranged to assess the mass centroid along at least one axis of the images or arrays of values and use this in the correction for instrumental effects.

22. Apparatus for assessing a property or properties of meat according to claim 20 wherein the associated computer system is arranged to assess the mass of the meat using the images or arrays of values and use this in the correction for instrumental effects.

23. Apparatus for assessing a property or properties of meat according to claim 20 wherein the associated computer system is arranged to assess the centroid along at least one axis of the images or arrays of values and use this in the correction for instrumental effects.

24. Apparatus for assessing a property or properties of meat according to claim 19 wherein the computer system arranged to process the images or arrays of values is further arranged to determine whether pixels in the image or data points in the array of values fall below a threshold level in the high x-ray intensity image or array of values.

25. Apparatus for assessing a property or properties of meat according to claim 24 wherein the computer system is arranged to process only pixels or data points in the high x-ray intensity image or array that fall below the threshold value.

26. Apparatus for assessing a property or properties of meat according to claim 19 wherein the computer system is arranged to grade the meat based on the assessed property or properties of the meat.

27. Apparatus for assessing a property or properties of meat according to claim 19 wherein the computer system is arranged to store the images and/or arrays of values with an identifier in a database for future retrieval and/or reprocessing.

28. Apparatus for assessing a property or properties of meat according to claim 19 wherein the property the associated computer system is arranged to assess is the chemical lean of the meat.

29. Apparatus for assessing a property or properties of meat according to claim 19 wherein the property the associated computer system is arranged to assess is the percentage fat of the meat.

30. Apparatus for assessing a property or properties of meat according to claim 19 wherein the property the associated computer system is arranged to assess is the weight of the meat.

31. Apparatus for assessing a property or properties of meat according to claim 19 wherein the property the associated computer system is arranged to assess is contamination of the meat.

32. Apparatus for assessing a property or properties of meat according to claim 19 wherein the property the associated computer system is arranged to assess is the tenderness of the meat.

33. Apparatus for assessing a property or properties of meat according to claim 32 wherein the computer system is further arranged to convert at least one red-green-blue image of the changes in atomic number into an intensity image and assess the meat tenderness from the at least one intensity image.

34. Apparatus for assessing a property or properties of meat according to claim 32 wherein the associated computer system is arranged to;

individually extract each component of a red-green-blue image of the changes in atomic number;

process each extracted component into an intensity image;

analyse each image to determine changes in image intensity;

produce a binary array for each component based on the changes in intensity; and assess meat tenderness from the variations of the binary arrays.

35. Apparatus for assessing a property or properties of meat according to claim 19 wherein the computer system is arranged to assess both the fat or chemical lean and weight.

36. Apparatus for assessing a property or properties of meat according to claim 19 wherein the computer system is arranged to assess both the fat or chemical lean and tenderness.

* * * * *

UNITED STATES PATENT AND TRADEMARK OFFICE
CERTIFICATE OF CORRECTION

PATENT NO. : 6,678,396 B2
DATED : January 13, 2004
INVENTOR(S) : Colin Murray Bartle It is certified that error appears in the above-identified patent and that said Letters Patent is hereby corrected as shown below:

<u>Title page,</u>
After Item [63], insert:

-- [30]     Foreign Application Priority Data

June 11, 2000        (NZ) ......................... 502,033 --

<u>Column 1,</u>
Line 6, after "Dec. 20, 2001" insert -- which claims benefit of priority from New Zealand Patent Application No. 502,033 filed June 11, 2000. --

Signed and Sealed this

Eighteenth Day of May, 2004

JON W. DUDAS
*Acting Director of the United States Patent and Trademark Office*